United States Patent

Kondo et al.

[11] 4,163,106
[45] Jul. 31, 1979

[54] PROSTAGLANDIN PRECURSORS AND PROCESSES FOR PREPARING THE SAME

[75] Inventors: Kiyosi Kondo, Yamato; Daiei Tunemoto, Sagamihara, both of Japan

[73] Assignee: Sagami Chemical Research Center, Tokyo, Japan

[21] Appl. No.: 772,053

[22] Filed: Feb. 25, 1977

[30] Foreign Application Priority Data

Feb. 25, 1976 [JP] Japan .................................. 51-18839
Feb. 25, 1976 [JP] Japan .................................. 51-18840
Feb. 27, 1976 [JP] Japan .................................. 51-20078
Feb. 27, 1976 [JP] Japan .................................. 51-20079
Mar. 1, 1976 [JP] Japan .................................. 51-21163

[51] Int. Cl.$^2$ .................... C07C 177/00; C07C 147/14
[52] U.S. Cl. .................................... 560/11; 260/402; 260/404; 560/9; 560/119; 560/121; 560/122; 562/429; 562/503
[58] Field of Search ............... 260/514 D, 514 J, 402, 260/404; 560/121, 122, 119, 9, 11; 562/503, 429

[56] References Cited

PUBLICATIONS

Kondo et al., Tet. Letters, 113 (1977).
Stewart et al., J. Organic Chem. 30, 1951 (1965).

Primary Examiner—Robert Gerstl
Attorney, Agent, or Firm—Sughrue, Rothwell, Mion, Zinn and Macpeak

[57] ABSTRACT

6-Alkenyl-bicyclo[3.1.0]hexanone compounds represented by the formula (I)

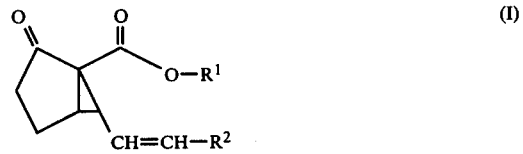

wherein $R^1$ represents an alkyl group having 1 to 4 carbon atoms or an aryl group, and $R^2$ represents a substituted or unsubstituted alkyl group having 1 to 8 carbon atoms;

cyclopentanone compounds represented by the formula (II)

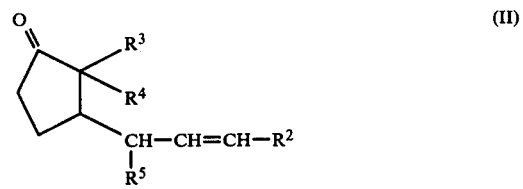

wherein $R^2$ is as defined above, $R^3$ represents a hydrogen atom or a —COOR$^1$ group wherein $R^1$ is as defined above, $R^4$ represents a hydrogen atom or a —CH$_2$—Y—(CH$_2$)$_n$—COOR$^6$ wherein Y represents a —CH$_2$CH$_2$— group or a —CH=CH— group, $R^6$ represents a hydrogen atom or an alkyl group having 1 to 4 carbon atoms, and n is an integer of 0 to 6, $R^5$ represents a —S—R$^7$ group or a —SO—R$^7$ group wherein $R^7$ represents an alkyl group having 1 to 4 carbon atoms or an aryl group, with the proviso that $R^3$ and $R^4$ cannot be hydrogen atoms at the same time, useful as prostaglandin precursors; and processes for preparing the same.

24 Claims, No Drawings

PROSTAGLANDIN PRECURSORS AND PROCESSES FOR PREPARING THE SAME

BACKGROUND OF THE INVENTION

1. Field of the Invention

This invention relates to prostaglandin precursors and processes for preparing the same. More particularly, this invention relates to 6-alkenyl-bicyclo[3.1.0-]hexanone compounds represented by the formula (I) hereinafter described and cyclopentanone compounds represented by the formula (II) hereinafter described which are useful as precursors for the synthesis of prostaglandin derivatives, and processes for preparing such prostaglandin precursors.

2. Description of the Prior Art

It is well known that the naturally-occurring prostaglandin compounds are composed of 20 carbon atoms and contain in the structure thereof a cyclopentanone ring and exist broadly in the brain, lung, kidney semen, uterus membrane, etc. of living body. These prostaglandin compounds are also known to have a wide variety of excellent pharmacological activities such as anti-ulcer, hypotensive, anti-asthmatic, uterotonic activities depending upon critical differences in the chemical structure of prostaglandin compounds, and recently the synthesis of prostaglandin compounds has been extensively studied.

Hitherto, in the synthesis of prostaglandin derivatives, the basic cyclopentanone structure is typically formed by (1) a method utilizing Dieckmann reaction as described, for example, in P. S. Pinkney, Or. Synthesis,- Coll. Vol1., 2, 116 (1943), (2) a method by Claisen condensation of 1,4-dicarbonyl compounds as described, for example, in R. A. Elison, Synthesis, 397 (1973) and (3) a method starting with cyclopentadiene as decribed, for example, in E. J. Corey et al., J. Amer. Chem. Soc. 93, 1489 (1971).

On the other hand, some of the conventional methods for the synthesis of prostaglandin derivatives employs a bicyclo[3.1.0]hexane compound as an intermediate as described, for example, in W. P Schneider, Chem. Commun., 304 (1969) and E. J. Corey et al., J. Amer. Chem. Soc., 94, 4014 (1972), but these methods are not considered to be practically useful since the ring-opening of the cyclopropane moiety contained in the above bicyclo[3.1.0]hexane compound takes place only in a low yield and the resulting compound is usually a mixture of diastereomers.

As is well known in the art, the basic structure of prostaglandin derivatives is composed of a cyclopentanone nucleus substituted with an alkyl group or an alkenyl group at the 2- or 3-position of the cyclopentanone nucleus. These side chains were conventionally introduced during the synthesis of prostaglandin derivatives.

More specifically, typical conventional procedures for introducing a side chain at the 3-position of the cyclopentanone nucleus comprise introducing an alkyl or alkenyl group by Michael type addition reaction, as described in C. J. Sih, et al., J. Amer. Chem. Soc., 94, 3643 (1972), and J. H. Fried, J. Amer. Chem. Soc., 94, 9256 (1972), or by reacting a carbonyl group contained in the substituent at the 3-position with a carbon anion to extend a chain length utilizing a carbon-carbon extension reaction, for example, by Wittig reaction, as described in E. J. Corey et al., J. Amer. Chem. Soc., 91, 5675 (1969).

Each of the above conventional processes has certain characteristic features, but is not considered advantageous procedures from the standpoint that it requires expensive and/or dangerous reagents, critical reaction donditions which are very difficult to be controlled, and isolation and purification of the desired product with considerable difficulty, and that the process generally has low selectivity of reaction thereby resulting in low yield of the desired product.

Further, it is well known that 3-(3'-hydroxy-1'-alkenyl)-cyclopentanone-2-carboxylic acid esters represented by the formula (IV) hereinafter described are useful as precursors for the synthesis of certain types of prostaglandin compounds (PGA$_2$) as described in, for example, J. Martel et al., Tetrahedron Lett., 1972, 149. The above 3-(3'-hydroxy-1'-alkenyl)cyclopentanone-2-carboxylic acid esters were conventionally prepared by intramolecular ring-opening reaction of vinyl-substituted epoxide compounds, but the synthesis of these epoxide compounds requires many reaction steps and, therefore, developments on more expedient and economical methods for producing the 3-(3'-hydroxy-1'-alkenyl)cyclopentanone-2-carboxylic acid esters have been strongly desired from the standpoint of the production of prostaglandin compounds on an industrial scale.

Recently, various methods for the synthesis of prostaglandin compounds have been developed, and one of the methods comprises rearrangement reaction of cyclopentanone sulfoxide compounds represented by the formula (IId) hereinafter described in the presence of a reagent having a thiophilicity, as described in G. Stork et al., J. Amer. Chem. Soc., 96, 6774 (1974). However, the method for the synthesis of the above cyclopentanone sulfoxide compounds used as precursors in the above rearrangement reaction taught in the above reference is not considered to be advantageous since this method requires various reaction steps, expensive reagents and very critical reaction conditions.

SUMMARY OF THE INVENTION

An object of the present invention is to provide novel 6-alkenyl-bicyclo[3.1.0]hexanone compounds represented by the formula (I)

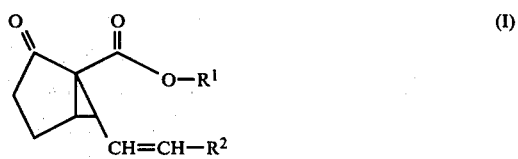

wherein $R^1$ represents an alkyl group having 1 to 4 carbon atoms or an aryl group, and $R^2$ represents a substituted or unsubstituted alkyl group having 1 to 8 carbon atoms; and novel cyclopentanone compounds represented by the formula (II)

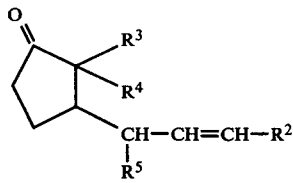
(II)

wherein $R^2$ is as defined above, $R^3$ represents a hydrogen atom or a —$COOR^1$ group wherein $R^1$ is as defined above, $R^4$ represents a hydrogen atom or a —$CH_2$—Y—$(CH_2)_n$—$COOR^6$ wherein Y represents a —$CH_2CH_2$— group or a —CH=CH— group, $R^6$ represents a hydrogen atom or an alkyl group having 1 to 4 carbon atoms, and n is an integer of 0 to 6, $R^5$ represents a -$S$-$R^7$ group or a-$SO$-$R^7$ group wherein $R^7$ represents an alkyl group having 1 to 4 carbon atoms or an aryl group, with the proviso that $R^3$ and $R^4$ cannot be hydrogen atoms at the same time.

Another object of this invention is to provide processes for preparing the above 6-alkenyl-bicyclo[3.1.0]hexanone compounds of the formula (I) and cyclopentanone compounds of the formula (II).

DETAILED DESCRIPTION OF THE INVENTION

As a result of extensive studies on the process for preparing prostaglandin and anlogues thereof, it was found that the precursors and the processes of the present invention provide expedient means for the synthesis of prostaglandin and derivatives thereof.

The term "alkyl group having 1 to 4 carbon atoms" as used herein for $R^1$, $R^6$ and $R^7$ means a straight or branched chain alkyl group having 1 to 4 carbon atoms and includes, for example, a methyl, ethyl, propyl, isopropyl, n-butyl, sec-butyl or tert-butyl group.

The term "substituted or unsubstituted alkyl group having 1 to 8 carbon atoms" as used herein for $R^2$ means a straight or branched alkyl group having 1 to 8 carbon atoms and includes, in addition to the examples of the alkyl group having 1 to 4 carbon atoms given above, a pentyl, hexyl, heptyl, octyl groups which may be substituted with an -O-alkyl group or a -S-alkyl group wherein the alkyl moiety can be a straight or branched chain and has 1 to 4 carbon atoms, or a phenoxy group which may be substituted with a halogen atom or an alkyl group having 1 to 4 carbon atoms.

The term "aryl group" as used herein for $R^1$ and $R^7$ means an unsubstituted or substituted phenyl group wherein the substituent is a halogen atom, an alkyl or alkoxy group having 1 to 4 carbon atoms.

The term "halogen" as used herein includes, fluorine, chlorine, bromine and iodine.

The cyclopentanone compounds represented by the formula (II) include the compounds represented by the formulae (IIa), (IIb), (IIc), (IId) and (IIe) given below.

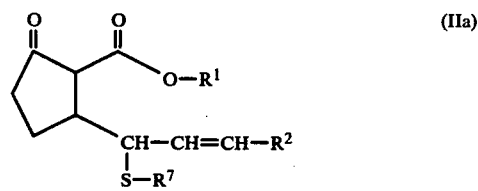
(IIa)

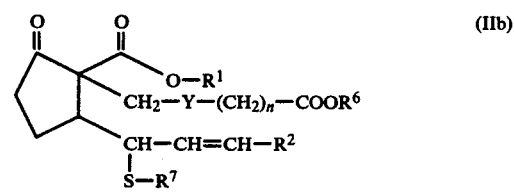
(IIb)

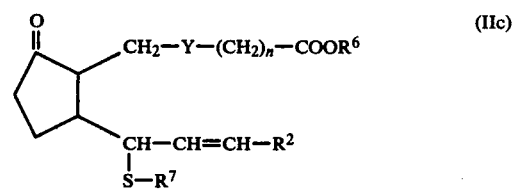
(IIc)

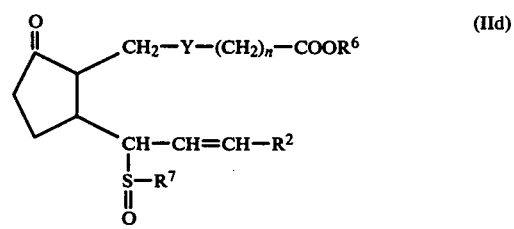
(IId)

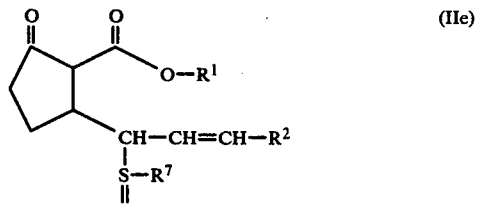
(IIe)

The 6-alkenyl-bicyclo[3.1.0]hexanone compounds of the formula (I) and cyclopentanone compounds of the formula (II) of the present invention can be prepared according to the processes shown in the Reaction Scheme below:

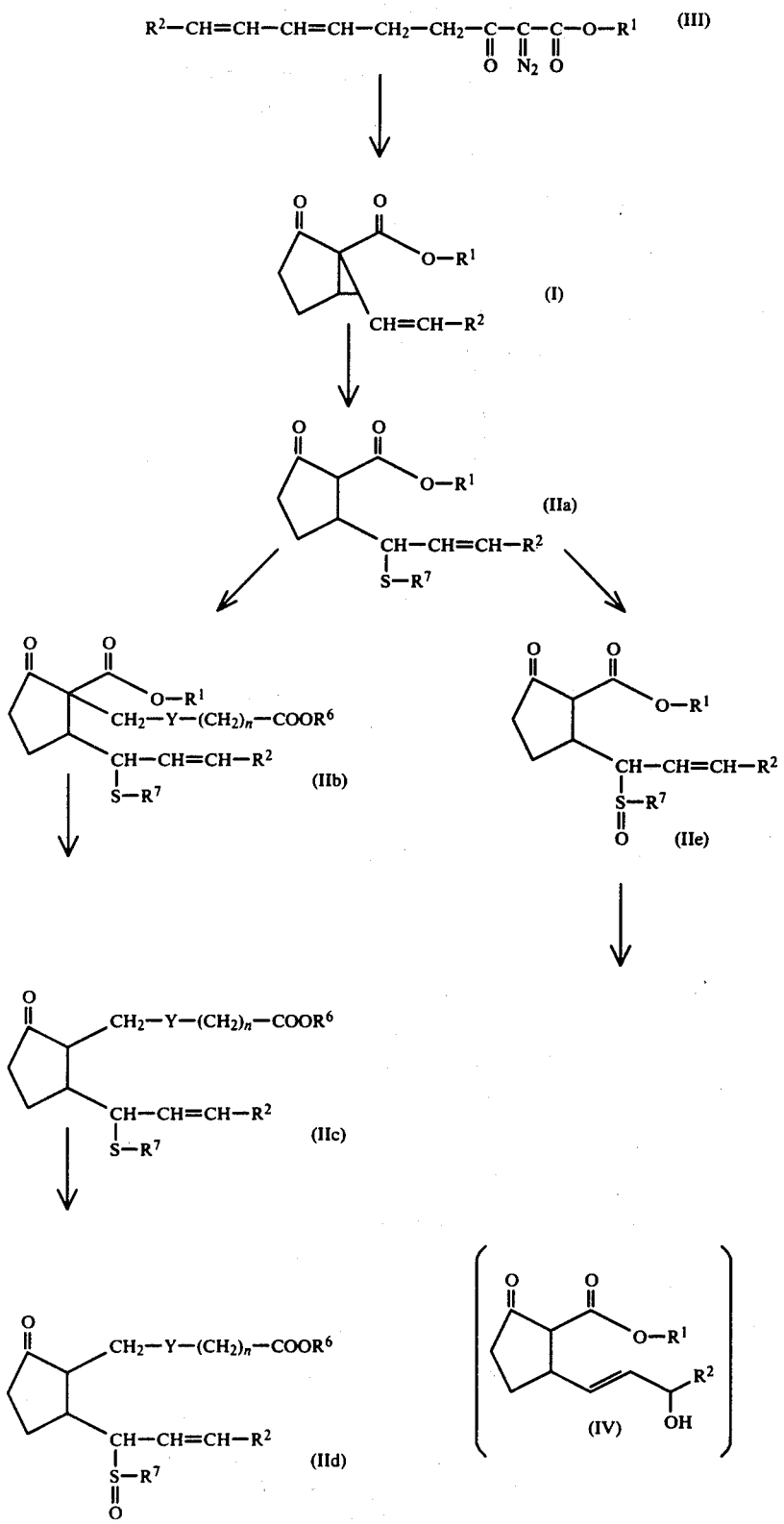
According to the present invention, there is provided a process for preparing a compound of the formula (IId)

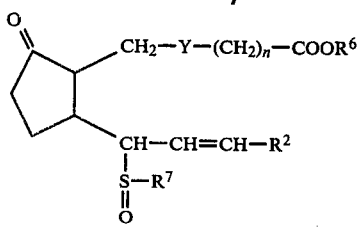
(IId)

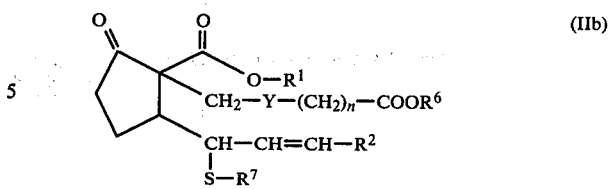
(IIb)

wherein $R^2$ represents a substituted or unsubstituted alkyl group having 1 to 8 carbon atoms, $R^6$ represents a hydrogen atom or an alkyl group having 1 to 4 carbon atoms, $R^7$ represents an alkyl group having 1 to 4 carbon atoms or an aryl group, Y represents a —CH$_2$CH$_2$—group or a —CH=CH— group, and n is an integer of 0 to 6, which comprises subjecting an α-diazo-β-keto ester compound of the formula (III)

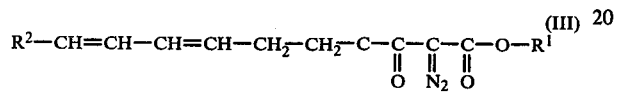
(III)

wherein $R^2$ is as defined above, and $R^1$ represents an alkyl group having 1 to 4 carbon atoms or an aryl group, to a carbene or carbenoid formation either by a catalytic reaction or a photodecomposition to produce a 6-alkenyl-bicyclo[3.1.0]hexanone compound of the formula (I)

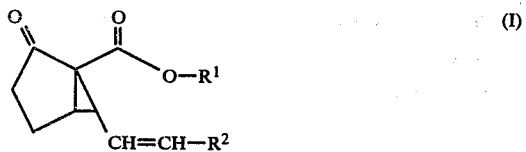
(I)

wherein $R^1$ and $R^2$ are as defined above, reacting the thus obtained 6-alkenyl-bicyclo[3.1.0]hexanone compound with a mercaptan compound of the formula (V)

$R^7$-SH (V)

wherein $R^7$ is as defined above, in the presence of a base to produce a cyclopentanone sulfide compound of the formula (IIa)

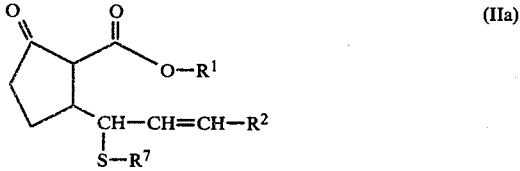
(IIa)

wherein $R^1$, $R^2$ and $R^7$ are as defined above, reacting the thus obtained cyclopentanone compound with an alkylating agent of the formula (VI)

Z-CH$_2$-Y-(CH$_2$)$_n$-COOR$^6$ (VI)

wherein $R^6$, Y and n are as defined above, and Z represents a halogen atom, a tosyloxy group or an acyloxy group, in the presence of a base to produce a compound of the formula (IIb)

wherein $R^1$, $R^2$, $R^6$, $R^7$, Y and n are as defined above, subjecting the thus obtained compound of the formula (IIb) to either (1) heat-treatment at a temperature of about 50° to 200° C. in the presence of an alkali metal compound and an inert polar solvent, or (2) an acid or alkali hydrolysis at a temperature of about 0° C. to about 150° C. followed by heat-treatment at a temperature of about 50° to about 200° C. to produce a compound of the formula (IIc)

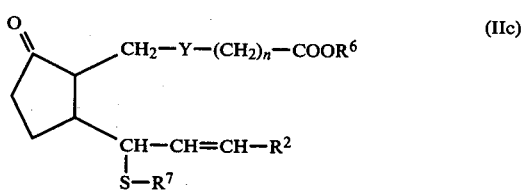
(IIc)

wherein $R^2$, $R^6$, $R^7$, Y and n are as defined above, and oxidizing the thus obtained compound of the formula (IIc) with an oxidizing agent in an inert solvent.

Also, the present invention provide a process for preparing a compound of the formula (IIe)

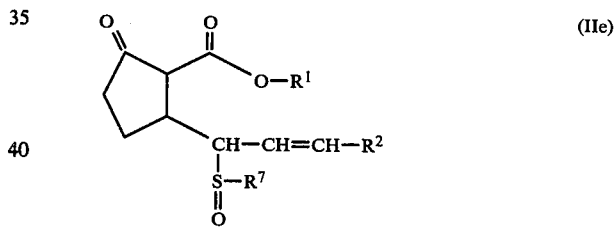
(IIe)

wherein $R^1$, $R^2$ and $R^7$ are as defined above, which comprises subjecting an α-diazo-β-keto ester compound of the above formula (III) to a carbene or carbenoid formation either by a catalytic reaction or a photodecomposition to produce a 6-alkenyl-bicyclo[3.1.0]hexanone compound of the above formula (I), reacting the thus obtained 6-alkenyl-bicyclo[3.1.0]hexanone compound with a mercaptan compound of the above formula (V) in the presence of a base to produce a cyclopentanone sulfide compound of the formula (IIa), and oxidizing the thus obtained cyclopentanone sulfide compound with an oxidizing agent in an inert solvent.

Further, the present invention provides a process for preparing a cyclopentanone sulfide compound having the formula (IIa) above, which comprises reacting a 6-alkenyl-bicyclo[3.1.0]-hexanone compound of the formula (I) above with a mercaptan compound having the formula (V) in the presence of a base.

The 6-alkenyl-bicyclo[3.1.0]hexanone compounds of the present invention having the formula (I) have an ester group at the 1-position and a carbonyl group at the 2-position and thus the cyclopropane ring of the compounds can easily be opened when these compounds are reacted with a nucleophilic reagent to produce selectively the corresponding cyclopentanone compound having the formula (II).

Generally, in the ring-opening and addition reaction between a vinyl-substituted-cyclopropane compound and a nucleophilic reagent, the unsaturated double bond of the vinyl moiety usually takes part in the reaction thereby giving rise to a so-called conjugated addition product, as described in J. M. Stewart et al., *J. Org. Chem.* 34, 7 (1969). However, in accordance with the process of this invention, it was found that the alkenyl group attached to the 6-position of the bicyclo compound of the formula (I) does not affect the above ring-opening and addition reaction thereby producing a cyclopentanone compound of the formula (IIa).

The cyclopentanone compounds of the formula (IIa) are very useful as precursors for producing prostaglandin compounds since they possess all the functional groups required for converting into prostaglandin compounds, i.e., an ester group at the 2-position and an allylic sulfide group at the 3-position of the cyclopentane ring.

More specifically, it is possible to introduce selectively an additional group at the 2-position of the cyclopentane ring since the ester group as an activating group is present at the 2-position, as illustrated hereinafter in detail for the production of compounds of the formula (IIb).

Further, an ester moiety of the activating group present at the 2-position can be removed easily and selectively after introduction of the additional group into the 2-position, as illustrated hereinafter in detail for the production of compounds of the formula (IIc).

Still further, the allylic sulfide group in the chain attached to the 3-position of the cyclopentane ring can easily be converted into an allylic alcohol moiety via oxidation and rearrangement reactions, as illustrated hereinafter in detail for the conversion of the compound of the formula (IIa)→(IIe)→(IV). The synthesis of prostaglandins using the compounds of the formula (IId) type was described in G. Stork et al., *J. Amer. Chem. Soc.*, 96, 6774 (1974) and, therefore, the compounds of the formula (IId) are useful as starting materials of prostaglandins.

Thus, the above characteristic features of the compounds and the processes of this invention can provide ideal synthetic procedures for producing side chains attached to the cyclopentane ring of the prostaglandin compounds.

The processes according to the present invention are further illustrated below in greater detail.

The starting materials represented by the formula (III) used in the present invention, $\alpha$-diazo-$\beta$-keto esters, can easily be prepared from commercially available raw materials such as acetoacetic acid esters and dienyl halides. For example, methyl 2-diazo-3-oxo-trans-6, trans-8-tetradecadienoate having the formula (III) wherein $R^1$ represents a methyl group and $R^2$ represents an n-pentyl group can be prepared by reacting methyl acetoacetate with 1-bromo-trans-2, trans-4-decadiene with a dianion according to the method described in, for example, L. Weiler et al., *J. Amer. Chem. Soc.*, 96, 1082 (1974) to form the corresponding methyl 3-oxo-trans-6, trans-8-tetradecadienoate and then diazotizing the resulting compound with a diazotizing agent in the presence of a base. In a similar manner, methyl 2-diazo-3-oxo-trans-6, trans-8-decadienoate of the formula (III) wherein $R^1$ represents a methyl group and $R^2$ represents a methyl group can be prepared from methyl acetoacetate and 1-bromo-trans-2, trans-4-hexadiene followed by diazotization as described above.

Suitable examples of diazotizing agents which can be used in the above diazotization are azide compounds such as tosyl azide, benzene-sulfonyl azide, phenyl azide, azidoformate and the like which are well known in the art.

Suitable examples of basic compounds which can be used in the above diazotization reaction are alkali metal hydroxides such as sodium hydroxide, potassium hydroxide and the like, alkali metal alkoxides such as sodium methoxide, sodium ethoxide, sodium t-butoxide, potassium t-butoxide and the like, and organic amines such as triethylamine, tributylamine, dimethylaniline, pyridine, piperidine and the like. Such basic compounds can preferably be used in an equimolar amount relative to the compound to be diazotized.

The diazotization reaction can be carried out in the absence of a solvent, but in order to produce the desired starting materials of the formula (III) in a high yield, it is preferred to use an inert organic solvent such as acetonitrile, dimethylformamide, tetrahydrofuran, alcohols, e.g., methanol, ethanol and the like, ethers, e.g., diethyl ether and the like, and halogenated hydrocarbons such as methylene chloride and the like. The diazotization generally proceed smoothly at room temperature (about 15° to 30° C.) without heating or cooling under atmospheric pressure.

The 6-alkenyl-bicyclo[3.1.0]hexanone compounds of the formula (I) can be prepared by subjecting an $\alpha$-diazo-$\beta$-keto ester compound of the formula (III) to carbene or carbenoid formation conditions by taking advantage of an intramolecular addition of the compound of the formula (III).

Generally, in carbene formation by decomposition of such diazo compounds, various reactions may occur and hence the reaction product can be expected to be a mixture of different products, but in accordance with the process of this invention, it is found that the compound of the formula (III) can be selectively converted into the desired 6-alkenyl-bicyclo[3.1.0]-hexanone of the formula (I).

The carbene or carbenoid formation can be achieved by either (1) a catalytic method or (2) a photodecomposition method.

The catalytic method can be achieved by catalyzing the starting material of the formula (III) in a trace amount of a catalyst such as a metal or a metal salt, for example, copper powder, copper bronze, copper halides, copper sulfate, acetylacetonate-copper, copper phosphine complex, silver oxide, silver nitrate and the like, in an inert atmosphere thereby obtaining a corresponding carbenoid.

The photodecomposition method can be achieved by exposing the starting material of the formula (III) to the light directly or through an inert atmosphere thereby obtaining a corresponding carbene. The light sources which can be used in the photodecomposition can be those usually employed in chemical industries, for example, low-pressure or high-pressure mercury lamps.

In both catalytic and photodecomposition methods, a solvent is not necessarily required, but the above methods can preferably be conducted using a solution of the starting material of the formula (III) in an inert solvent and in an inert atmosphere in order to minimize the formation of byproducts and to improve the reaction selectively to the desired product. Typically, the above methods can be advantageously carried out in an inert atmosphere such as nitrogen or argon gas and in an inert solvent such as benzene, toluene, xylene, hexane, petroleum ether and the like.

The carbene or carbenoid formed as described above immediately gives rise to cyclization selectively with the double bond present in the molecule thereof to produce a 6-alkenyl-bicyclo[3.1.0]hexanone compound represented by the formula (I) in high yield.

Typical examples of the 6-alkenyl-bicyclo[3.1.0]-hexanone compounds of the formula (I) thus formed are methyl exo-6-(trans-1'-heptenyl)-2-oxo-bicyclo[3.1.0]hexane-1-carboxylate, ethyl exo-6-(trans-1'-heptenyl)-2-oxo-bicyclo-[3.1.0]hexane-1-carboxylate, methyl exo-6-(trans-1'-propenyl)-2-oxo-bicyclo[3.1.0]hexane-1-carboxylate, and ethyl exo-6-(trans-1'-propenyl)-2-oxo-bicyclo[3.1.0]hexane-1-carboxylate and the like.

The 6-alkenyl-bicyclo[3.1.0]hexanone compounds of the formula (I) obtained as above can then be converted into the corresponding cyclopentanone compounds of the formula (IIa) by ring-opening of the cyclopropyl group present in the molecule through a reaction with a mercaptan compound of the formula (V)

$$R^7\text{-SH} \quad (V)$$

wherein $R^7$ represents an alkyl group having 1 to 4 carbon atoms or an aryl group, in the presence of a base to form a compound of the formula (IIa).

The reaction between a 6-alkenyl-bicyclo[3.1.0]hexane compound of the formula (I) and a mercaptan compound of the formula (V) can be carried out at a temperature of about 0° to about 100° C., preferably at room temperature, using preferably an approximately equimolar amount of the mercaptan compound and the compound of the formula (I) in the presence of a base. A larger amount of the mercaptan compound over the equimolar amount can be used without causing any adverse affect.

Suitable examples of bases which can be used in the above reaction are alkali metal hydroxides such as potassium hydroxide, sodium hydroxide and the like, alkali metal alkoxides such as sodium methoxide, potassium methoxide, sodium ethoxide, potassium t-butoxide and the like, and organic amines such as triethylamine, tributylamine, pyridine and the like.

A so-called catalytic amount of the base is generally sufficient, but the use of an approximately equimolar amount of the base relative to the compound of the formula (I) is preferred for reducing the reaction time required for completing the reaction and also increasing the yield of the desired product of the formula (IIa).

The base used in the above reaction is considered to react at the first stage with a mercaptan compound of the formula (V) in the reaction system to produce a mercaptide anion. The mercaptide anion thus formed appears to attack the bicyclo nucleus of the compound of the formula (I) thereby resulting in a partial ring-opening of the bicyclo nucleus to produce a salt comprising an anion of the compound of the formula (IIa) and the anion is then converted into a compound of the formula (IIa), as illustrated below where an alkali metal hydroxide (MOH, M is an alkali metal) is used as a base.

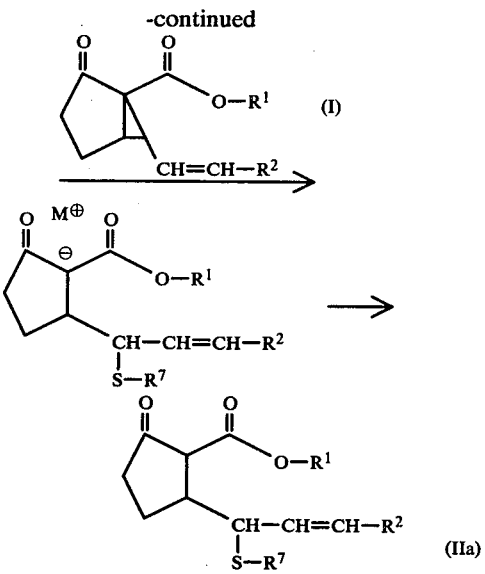

As is apparent to one skilled in the art, a mercaptide anion corresponding to the mercaptan compound of the formula (V) also has the same function as the mercaptan compound, and thus the present invention also includes the use of such mercaptide anions in the reaction with the compound of the formula (I)

In carrying out the reaction between the 6-alkenyl-bicyclo[3.1.0]hexanone compound of the formula (I) and the mercaptan compound of the formula (V), it is preferred to use a polar solvent which does not take part in the reaction and which is inert to the reactants used as well as to the desired product. Suitable examples of polar solvents are ethers such as diethyl ether, tetrahydrofuran and the like, alcohols such as methanol, ethanol, t-butanol and the like, dimethylformamide, acetonitrile, dimethyl sulfoxide and the like.

The cyclopentanone sulfide compound of the formula (IIa) thus obtained has a characteristic feature in that it easily reacts with an alkylating agent at the 2-position due to the presence of an activating ester group.

Representative compounds of the cyclopentanone sulfide compounds of the formula (IIa) are methyl 2-oxo-5-(1'-phenylthio-trans-2'-butenyl)cyclopentane-1-carboxylate, methyl 2-oxo-5-(1'-phenylthio-trans-2'-octenyl)cyclopentane-1-carboxylate, ethyl 2-oxo-5-(1'-phenylthio-trans-2'-octenyl)cyclopentane-1-carboxylate, methyl 2-oxo-5-(1'-tolylthio-trans-2'-octenyl)-cyclopentane-1-carboxylate, methyl 5-(1'-methylthio-trans-2'-octenyl)-2-oxo-cyclopentane-1-carboxylate, methyl 5-(4'-methyl-1'-phenylthio-trans-2'-octenyl)-2-oxo-cyclopentane-1-carboxylate, etc.

The compound of the formula (IIb) can then prepared from the cyclopentanone sulfide compound of the formula (IIa) obtained as above by reacting the cyclopentanone sulfide compound with an alkylating agent represented by the formula (VI)

$$Z-CH_2-Y-(CH_2)_n-COOR^6 \quad (VI)$$

wherein Z represents a halogen atom, a tosyloxy group or an acyloxy group, Y represents a $-CH_2CH_2-$ group or a $-CH=CH-$ group, $R^6$ represents a hydrogen atom or an alkyl group having 1 to 4 carbon atoms, and n is an integer of from 0 to 6, in the presence of a base.

The reaction between the cyclopentanone sulfide compound of the formula (IIa) and the alkylating agent of the formula (VI) can be carried out at a temperature of from about −80° to about 150° C., preferably at room temperature (about 15° to 30° C.) using an approximately equimolar amount of the alkylating agent of the formula (VI) relative to the compound of the formula (IIa), for a period of from about 1 to aboout 24 hours. A larger or smaller amount of the alkylating agent can be used, but no additional advantages can be realized.

Representative alkylating agents of the formula (VI) which can be used in the above alkylation are methyl 7-chloroheptanoate, methyl 7-bromoheptanoate, methyl 7-iodoheptanoate, ethyl 7-iodoheptanoate, methyl 7-bromo-5-heptenoate, methyl 7-iodo-5-heptenoate, 1-iodo-6-(2′-tetrahydropyranyloxycarbonyl)-hexane and the like.

Suitable examples of bases which can be used in the above alkylation reaction are alkali metal carbonates such as potassium carbonate, sodium carbonate and the like, alkali metal hydroxides such as potassium hydroxide, sodium hydroxide and the like, alkali metal hydrides such as sodium hydride, potassium hydride and the like, alkali metal alkoxides such as sodium methoxide, potassium methoxide, sodium ethoxide, potassium t-butoxide and the like, and organic amines such as triethylamine, tributylamine, pyridine and the like. These bases can be used in an amount of approximately equimolar amount to slightly molar excess amount, for example, about 1.2 to 3.0 mols, per mol of the compound of the formula (IIa).

The alkylation reaction described above is advantageously carried out in an inert organic solvent which does not take part in the reaction and which is inert to the reactants as well as the desired compound. Suitable examples of solvents are alcohols such as methanol, ethanol, t-butanol and the like, ethers such as diethyl ether, tetrahydrofuran and the like, benzene, toluene, xylene, dimethylformamide, acetonitrile, dimethyl sulfoxide and the like.

Representative cyclopentanone sulfide compounds of the formula (IIb) are methyl 1-(6′-methoxycarbonylhexyl)-2-oxo-5-(1′-phenylthio-2′-trans-octenyl)cyclopentane-1-carboxylate, methyl 1-(6′-methoxycarbonyl-2′-hexenyl)-2-oxo-5-(1′-phenylthio-trans-octenyl)cyclopentane-1-carboxylate, methyl 1-(6′-ethoxycarbonylhexyl)-2-oxo-5-(1′-tolylthio-trans-2′-octenyl)-cyclopentane-1-carboxylate, methyl 1-(6′-methoxycarbonylhexyl)-5-(4′-methyl-1′-phenylthio-trans-2′-octenyl)-2-oxo-cyclopentane-1-carboxylate, methyl 1-(6′-methoxycarbonylhexyl)-5-(1′-methylthio-trans-2′-octenyl)-2-cyclopentane-1-carboxylate, etc.

The compound of the formula (IIc) can be prepared from the compound of the formula (IIb) by removal of the alkoxycarbonyl group attached to the 2-position of the cyclopentane ring.

The removal of the alkoxycarbonyl group can be achieved by one of alternative procedures, i.e., (1) heat-treatment of the compound of the formula (IIb) in the presence of an alkali metal salt or (2) acid or alkali hydrolysis followed by heat-treatment.

The heat-treatment as described in (1) above can be effected at a temperature of about 50° to about 200° C., preferably 100° to 150° C., for a period of from about 30 minutes to about 3 hours, preferably in the presence of an inert polar solvent which does not take part in the reaction, for example, alcohols such as methanol, ethanol, t-butanol and the like, ethers such as diethyl ether, tetrahydrofuran and the like, amines such as pyridine, piperidine, colidine and the like, dimethylformamide, acetonitrile, dimethyl sulfoxide and the like. The time required for completing the removal of the alkoxycarbonyl group varies widely depending upon the type of the compound of the formula (IIb) and the alkali metal salt used as well as the temperature employed in the heat-treatment.

Suitable examples of alkali metal salts which can be used in the above heat-treatment (1) are alkali metal iodides and hydrates thereof such as sodium iodide, potassium iodide, lithium iodide and hydrates thereof, and alkali metal cyanides such as sodium cyanide, potassium cyanide, lithium cyanide and the like. Particularly preferred alkali metal salts from the standpoint of high yield of the desired product are lithium iodide or the hydrate thereof and sodium cyanide. The alkali metal salts can be used in an approximately equimolar amount relative to the compound of the formula (IIb) with a satisfactory result, but a larger or smaller amount of the alkali metal salts may be used.

In an alternative procedure for the removal of the alkoxycarbonyl group by acid or alkali hydrolysis, various acids or bases can be used. Examples of acids which can be used in the acid hydrolysis are inorganic acids such as hydrochloric acid, sulfuric acid, phosphoric acid and the like, and organic acids such as p-toluenesulfonic acid, acetic acid and the like. Examples of bases which can be used for the alkali hydrolysis are alkali metal hydroxides such as sodium hydroxide, potassium hydroxide and the like, alkali metal carbonates such as sodium carbonate, potassium carbonate and the like. The acid can be used in a so-called catalytic amount in the acid hydrolysis, but the base can be preferably used in an approximately equimolar amount relative to the compound of the formula (IIb).

The acid and alkali hydrolysis can be effected at a temperature of about 0° to about 150° C., preferably 50° to 100° C., for about 1 to about 24 hours, preferably 2 to 5 hours.

Under hydrolysis conditions using an acid, the hydrolysis of an ester group and the decarboxylation can be achieved simultaneously by heating the reaction system at the temperature set forth above, whereas under hydrolysis conditions using a base, only the ester group is removed and the resulting hydrolysis reaction mixture should be rendered neutral or weakly acidic and then subjected to the heat-treatment for decarboxylation. In either cases, the time required for heat-treatment varies depending upon the type of the compound to be treated and the temperature used, but heating for about 30 minutes to about 3 hours is generally sufficient.

The removal of alkoxycarbonyl group by acid or alkali hydrolysis can be preferably effected in an aqueous medium such as water, or a hydrated solvent such as hydrated tetrahydrofuran, acetone, alcohols and the like.

Typical examples of the compounds of the formula (IIc) thus obtained are 2-(6′-methoxycarbonylhexyl)-3-(1′-phenylthio-2′-trans-octenyl)cyclopentanone, 2-(6′-methoxycarbonyl-2′-hexenyl)-3-(1′-phenylthio-trans-2′-octenyl)cyclopentanone, 2-(6′-enthoxycarbonylhexyl)-3-(1′-tolylthio-trans-2′-octenyl)-cyclopentanone, 2-(6′-methoxycarbonylhexyl)-3-(4′-methyl-1′-phenylthio-2′-trans-octenyl)cyclopentanone, 2-(6′-methoxycarbonylhexyl)-3-(1'-methylthio-trans-2'-octenyl)cyclopentanone, etc.

The compounds of the formula (IId) and (IIe) can be prepared from the corresponding cyclopentanone sulfide compounds of the formulae (IIc) and (IIa), respectively, by oxidation using an oxidizing agent in an inert solvent at a temperature of about −80° to about 100° C., preferably at room temperature, for about 1 to about 24 hours.

Suitable examples of oxidizing agents which can be used for the above oxidation are inorganic oxidizing agents such as sodium iodate, hydrogen peroxide, oxygen, ozone, manganese dioxide, selenium dioxide, chromic acid, nitric acid, dinitrogen tetraoxide and the like, and organic oxidizing agents such as peracetic acid, perbenzoic acid, m-chloroperbenzoic acid, iodosobenzene and the like. Preferred organic oxidizing agents are organic peroxides described above, more preferably, m-chloroperbenzoic acid, since these peroxides do not adversely affect reactive groups present in the cyclopentanone sulfide compounds of the formulae (IIc) and (IIa), such as a carbonyl group and an ester group. The oxidizing agent can be used in an approximately equimolar amount relative to the compound of the formula (IIc) or (IIa).

Suitable examples of inert solvents are water, alcohols such as methanol, ethanol and the like, ethers such as diethyl ether, tetrahydrofuran, dimethoxyethane and the like, acetic acid, chloroform, methylene chloride, benzene and the like, but other inert solvents which do not take part in the oxidation and which do not adversely affect the compounds of the formulae (IId) and (IIe) as well as the desired products can be used as well.

Typical examples of compounds of the formula (IId) thus obtained are 3-(1'-benzenesulfinyl-trans-2'-octenyl)-2-(6'-methoxycarbonylhexyl)cyclopentanone, 3-(1'-benzenesulfinyl-trans-2'-octenyl)-2-(6'-methoxycarbonyl-2'-hexenyl)cyclopentanone, 3-(1'-benzenesulfinyl-2'-trans-octenyl)-2-(6'-ethoxycarbonylhexyl)cyclopentanone, 3-(1'-benzenesulfinyl-4'-methyl-trans-2'-octenyl)-2-(6'-methoxycarbonylhexyl)cyclopentanone, 3-(1'-methanesulfinyl-trans-2'-octenyl)-2-(6'-methoxycarbonylhexyl)-cyclopentanone, etc.

Typical examples of compounds of the formula (IIe) thus obtained are methyl 2-oxo-5-(1'-benzenesulfinyl-trans-2'-octenyl)cyclopentane-1-carboxylate, ethyl 2-oxo-5-(1'-benzenesulfinyl-trans-2'-octenyl)cyclopentane-1-carboxylate, methyl 2-oxo-5-(1'-toluenesulfinyl-trans-2'-octenyl)cyclopentane-1-carboxylate, methyl 2-oxo-5-(1'-methanesulfinyl-trans-2'-octenyl)cyclopentane-1-carboxylate, etc.

The compounds of the formulae (IId) and (IIe) thus obtained can be converted into the corresponding prostaglandin derivatives by treating the compounds with a reagent having "thiophilicity", i.e., a reagent having a high affinity for a sulfur atom, for example, organic amines such as triethylamine, diethylamine, pyridine and the like, organophosphorus compounds such as trimethyl phosphite, triethyl phosphite, trisdimethylaminophosphine and the like, and mercaptans, in an approximately equimolar amount relative to the compound of the formula (IId) or (IIe), at a temperature of from about −30° C. to room temperature for about 2 to about 24 hours in an inert solvent such as alcohols, for example, methanol, ethanol, t-butanol and the like, ethers such as diethyl ether, tetrahydrofuran and the like, dimethyl sulfoxide, hexamethylphosphoric triamide and the like. For example, one mol of methyl 2-oxo-5-(1'-benzenesulfinyl-trans-2'-octenyl)cyclopentane-1-carboxylate in absolute methanol is treated with about 2 mols of trimethyl phosphite at room temperature for about 3 hours to obtain methyl 5-(3'-hydroxy-trans-1'-octenyl)-2-oxo-cyclopentane-1-carboxylate of the formula (IV), as illustrated in Reference Example 5 hereinafter described.

The present invention is further illustrated by the following Reference Examples and Examples, but these examples are given for illustrative purposes only and are not to be construed as limiting the present invention. Unless otherwise indicated, all percents, ratios, parts and the like are by weight.

REFERENCE EXAMPLE 1

575 mg (24 mmols) of sodium hydride was suspended in 50 ml of anhydrous tetrahydrofuran in an argon atmosphere according to the procedure described in L. Weiler et al., *J. Amer. Chem. Soc.*, 96, 1082 (1974). 28 g (24 mmols) of methyl acetoacetate was dissolved in 10 ml of tetrahydrofuran under cooling at 0° C. with stirring and the resulting was added to the above prepared suspension. After 10 minutes, a solution of n-butyl lithium (24 mmols) in n-hexane was added dropwise to the mixture. After completion of the addition, the resulting reaction mixture was allowed to stand for 15 minutes and cooled to −75° C. followed by addition of a solution of 5.14 g (23.7 mmols) of 1-bromo-trans-2, trans-4-decadiene dissolved in 10 ml of tetrahydrofuran. The mixture was stirred at that temperature for 30 minutes and then allowed to warm slowly to room temperature followed by stirring for 3 hours. The mixture was then worked up in a usual manner, and the oily substance which remained was subjected to distillation under reduced pressure to obtain 4.02 g (67% yield) of methyl 3-oxo-trans-6, trans-8-tetradecadienoate as an oily substance having a boiling point of 123°–128° C./0.5 mmHg.

Infrared Absorption Spectrum (cm$^{-1}$): 1755, 1725, 1665, 1630, 1240, 1155, 990.

REFERENCE EXAMPLE 2

910 mg (3.6 mmols) of methyl 3-oxo-trans-6, trans-8-tetradecadienoate and 404 mg (4 mmols) of triethylamine were dissolved in 30 ml of acetonitrile and a solution of 730 mg (3.7 mmols) of p-toluenesulfonyl azide dissolved in 3 ml of acetonitrile was added to the solution while cooling at room temperature. After stirring for 3 hours, the solvent was removed by distillation and the resulting residue was diluted with 50 ml of diethyl ether. The solution was then washed repeatedly with a 5% aqueous solution of potassium hydroxide until the aqueous layer became colorless and finally with a saturated aqueous solution of sodium chloride. The ether layer was dried over anhydrous magnesium sulfate, filtered and concentrated under reduced pressure to obtain 1.10 g (100% yield) of methyl 2-diazo-3-oxo-trans-6, trans-8-tetradecadienoate as a yellow oily substance.

Infrared Absorption Spectrum (cm$^{-1}$): 2125, 1725, 1655, 990.

REFERENCE EXAMPLE 3

In the same manner as described in Reference Example 1 but using 660 mg (27.5 mmols) of sodium hydride, 3.19 g (27.5 mmols) of methyl acetoacetate, 17.6 ml of a solution of n-butyl lithium in hexane (27.5 mmols) and 4.53 g (27.5 mmols) of 1-bromo-trans-2, trans-8-hexadiene as starting materials, 4.04 g (75% yield) of methyl 3-oxo-trans-6, trans-8-decadienoate was obtained as an oily substance having a boiling point of 93°–96° C./0.5 mmHg. Infrared Absorption Spectrum (cm$^{-1}$): 1750, 1720, 1655, 1625, 990.

REFERENCE EXAMPLE 4

In the same manner as described in Reference Example 2 but using 3.34 g (17 mmols) of methyl 3-oxo-trans-6, trans-8-decadienoate, 1.72 g (17 mmols) of triethylamine and 3.36 g (17 mmols) of p-toluenesulfonyl azide as starting materials, 3.46 g (92% yield) of methyl 2-diazo-3-oxo-trans-6, trans-8-decadienoate was obtained as a yellow oily substance.

Infrared Absorption Spectrum (cm$^{-1}$): 2120, 1755, 1730, 990, 965.

EXAMPLE 1

4.78 g (17.5 mmols) of methyl 2-diazo-3-oxo-trans-6, trans-8-tetradecadienoate was dissolved in 50 ml of benzene and 460 mg of an acetylacetone-copper complex was added to the solution. The mixture was then heated while refluxing and stirring overnight in an argon atmosphere. Most of benzene was removed under reduced pressure, and 70 ml of diethyl ether was added to the resulting residue. The precipitate formed was filtered and the filtrate was concentrated under reduced pressure. The concentrate was purified by silica gel column chromatography using a mixture of ethyl acetate and n-hexane (1:9 by volume) as an eluent to obtain 2.56 g (62% yield) of methyl exo-6-(trans-1'-heptenyl)-2-oxo-bicyclo[3.1.0]hexane-1-carboxylate as an oily substance.

Infrared Absorption Spectrum (cm$^{-1}$): 1755, 1730, 970.

NMR Absorption Spectrum (CCl$_4$) δ: 0.85 (t, J=6 Hz, 3H), 1.08–1.54 (m, 6H), 1.80–2.59 (m, 8H), 3.64 (s, 3H), 5.11 (dd, J=15 Hz, J=8 Hz, 1H), 5.61 (dt, J=15 Hz, J=7 Hz, 1H).

EXAMPLE 2

1.39 g (5 mmols) of methyl 2-diazo-3-oxo-trans-6, trans-8-tetradecadienoate was dissolved in 50 ml of benzene and 1 g of anhydrous copper sulfate was added to the solution. The mixture was then heated while refluxing and stirring overnight in an argon atmosphere. After allowing the mixture to cool, the mixture was filtered and the filtrate was concentrated under reduced pressure. The resulting residue was purified by subjecting it to silica gel chromatography using a mixture of ethyl acetate and n-hexane (1:9 by volume) as an eluent to obtain 660 mg (53% yield) of methyl exo-6-(trans-1'-heptenyl)-2-oxo-bicyclo[3.1.0]hexane-1-carboxylate as an oily substance.

EXAMPLE 3

3.46 g (15.6 mmols) of methyl 2-diazo-3-oxo-trans-6, trans-8-decadienoate was dissolved in 60 ml of benzene and 3.5 g of anhydrous copper sulfate was added to the solution. The mixture was then heated while refluxing and stirring for 6 hours. After allowing the mixture to cool, the precipitate formed was filtered using Celite as a filter aid and the filtrate was concentrated under reduced pressure. The resulting residue was distilled under reduced pressure to obtain 1.95 g (64% yield) of methyl exo-6-(trans-1'-propenyl)-2-oxo-bicyclo[3.1.0]hexane-1-carboxylate as an oily substance.

Infrared Absorption Spectrum (cm$^{-1}$): 1755, 1730, 985, 960

NMR Absorption Spectrum (CCl$_4$) δ: 1.65 (dd, J=1.5 Hz, J=6.5 Hz, 3H), 1.82 - 2.64 (m, 6H), 3.66 (s, 3H), 5.14 (q of dd, J=1.5 Hz, J=8.5 Hz, J=15.5 Hz, 1H), 5.64 (dq, J=6.5 Hz, J=15.5 Hz, 1H).

EXAMPLE 4

0.5 g (4.5 mmols) of potassium t-butoxide was dissolved in 40 ml of t-butyl alcohol, and a solution of 0.68 g (6.2 mmols) of thiophenol dissolved in 3 ml of t-butyl alcohol was added to the solution. The mixture was stirred at room temperature for 15 minutes, and a solution of 1.01 g (4.03 mmols) of methyl exo-6-(trans-1'-heptenyl)-2-oxo-bicyclo[3.2.0]hexane-1-carboxylate dissolved in 5 ml of t-butyl alcohol was added to the mixture. The resulting mixture was then stirred at room temperature for 1 hour at most of the solvent was removed under reduced pressure. Diethyl ether was added to the residue and the mixture was then rendered acidic with dilute hydrochloric acid followed by extraction with diethyl ether. The ethereal layer was washed with a saturated aqueous solution of sodium chloride, dried over anhydrous magnesium sulfate and filtered. The filtrate was concentrated and the residue was purified by silica gel column chromatography using a mixture of ethyl acetate and n-hexane (1:9 by volume) to obtain 1.29 g (89% yield) of methyl 2-oxo-5-(1'-phenylthio-trans-2'-octenyl)cyclopentane-1-carboxylate.

Infrared Absorption Spectrum (cm$^{-1}$): 1765, 1735, 1665, 1620, 975.

Mass Spectrum m/e: 360, 219.

EXAMPLE 5

In the same manner as described in Example 4 but using 112 mg (1 mmol) of potassium t-butoxide, 110 mg (1 mmol) of thiophenol and 194 mg (1 mmol) of methyl exo-6-(trans-1'-propenyl)-2-oxo-bicyclo[3.1.0]hexane-1-carboxylate as starting materials, 210 mg (70% yield) of methyl 2-oxo-5-(1'-phenylthiotrans-2'-butenyl)cyclopentane-1-carboxylate was obtained as an oily substance.

Infrared Absorption Spectrum (cm$^{-1}$): 1760, 1730, 1660, 1620, 965.

NMR Absorption Spectrum (CCl$_4$): 1.53 (d, J=4 Hz, 3H), 1.90–2.72 (m, 5H), 2.72–3.25 (m, 1H), 3.60 (s, 3H), 3.25–3.83 (m, 1H), 4.80–5.73 (m, 2H), 6.93–7.70 (m, 5H).

EXAMPLE 6

A 25% of suspension of 0.75 g (4.64 mmols) of potassium hydride was washed with n-hexane in an argon atmosphere to remove the oil. n-Hexane was then removed under reduced pressure and the residue was cooled in a water bath. 6 ml of dimethyl sulfoxide was added slowly to the residue while stirring to prepare a solution of dimsyl sodium. A solution of 1.67 g (4.64 mmols) of methyl 2-oxo-5-(1'-phenylthio-trans-2'-octenyl)cyclopentane-1-carboxylate in 3 ml of dimethyl sulfoxide was added to the above solution. After allowing the mixture to sand for 15 minutes, a solution of 1.25 g (4.64 mmols) of methyl 7-iodoheptanoate dissolved in 2 ml of dimethyl sulfoxide

EXAMPLE 7

In the similar manner as described in Example 6, but using 1.85 g (10 mmols) of potassium hydride, 3.6 g (10 mmols) of methyl 2-oxo-5-(1'-phenylthio-trans-2'octenyl)-cyclopentane-1-carboxylate and 3.1 g (11 mmols)

of ethyl 7-iodoheptanoate as starting materials, 3.35 g (65% yield) of methyl 1-(6'-ethoxycarbonyl)-2-oxo-5-(1'-phenylthio-trans-2'-octenyl)cyclopentane-1-carboxylate was obtained as a viscous oil.

Infrared Absorption Spectrum (cm$^{-1}$): 1754, 1735, 1170, 965, 750 690.

NMR Absorption Spectrum (CCl$_4$): 0.82 (t, J=6 Hz, 3H), 0.98–2.60 (m, 25H), 1.20 (t, J=6 Hz, 3H), 3.36–3.64 (m, 1H), 3.56 (s, 3H), 4.00 (q, J=6 Hz, 2H), 4.72–5.28 (m, 2H), 7.02–7.44 (m, 5H).

EXAMPLE 8

1.05 g (2.1 mmols) of methyl 1-(6'-methoxycarbonylhexyl)-2-oxo-5-(1'-phenylthiomethyl-trans-2'-octenyl)-cyclopentane-1-carboxylate was dissolved in 4 ml of hexamethylphosphoric triamide and 200 mg (4 mmols) of sodium cyanide was added to the solution followed by heating at a temperature of 80° C. for 2 hours while stirring. After allowing the mixture to cool, diluted hydrochloric acid was added and the was extracted with ethyl acetate. The ethyl acetate layer was washed with a saturated aqueous solution of sodium chloride and dried over anhydrous magnesium sulfate. The mixture was then filtered and the solvent was removed from the filtrate under reduced pressure. The resulting residue was purified by silica gel column chromatography using a mixture of ethyl acetate and n-hexane as an eluent to obtain 580 mg (63% yield) of 2-(6'-methoxycarbonylhexyl)-3-(1'-phenylthio-trans-2'-octenyl)cyclopentanone as a viscous oily substance.

Infrared Absorption Spectrum (cm$^{-1}$); 1740, 1720, 970.

NMR Absorption Spectrum (CCl$_4$) δ: 0.83 (t, J=6 Hz, 3H), 0.98–2.40 (m, 25H), 3.40–3.70 (m, 1H), 3.54 (s, 3H), 5.08–5.38 (m, 2H), 6.96–7.50 (m, 5H).

EXAMPLE 9

In the similar manner as described in Example 8, but using 800 mg (19 mmols) of lithium chloride and 1.95 g (3.88 mmols) of methyl 1-(6-methoxycarbonyl hexyl)-2-oxo-5-(1'-phenyl-thiomethyl-trans-2'-octenyl)cyclopentane-1-carboxylate as starting materials and conducting the reaction at a temperature of 100° C. for 6 hours, 1.58 g (92% yield) of 2-(6'-methoxycarbonylhexyl)-3-(1'-phenylthio-trans-2'-octenyl)cyclopentanone was obtained as a viscous oil.

EXAMPLE 10

In the similar manner as described in Example 8, but using 100 mg (2.4 mmols) of lithium chloride and 200 mg (0.39 mmol) of methyl 1-(6'-ethoxycarbonyl)-2-oxo-5-(1'-phenylthiotrans-2'-octenyl)cyclopentane-1-carboxylate as starting materials and conducting the reaction at a temperature of 100° C. for 6 hours, 143 mg (80% yield) of 2-(6'-ethoxycarbonylhexyl)-3-(1'-phenylthio-trans-2'-octenyl)cyclopentanone was obtained as a viscous oil.

Infrared Absorption Spectrum (cm$^{-1}$): 1740, 1583, 1462, 1174, 970.

NMR Absorption Spectrum (CCl$_{94-}$) δ: 0.82 (t, J=6 Hz, 3H), 0.95 - 0.60 (m, 29H), 3.30–3.64 (m, 1H), 3.90 (q, J=6 Hz, 2H), 4.98–5.50 (m, 2H), 6.94–7.45 (m, 5H).

EXAMPLE 11

360 mg (1 mmol) of methyl 2-oxo-5-(1'-phenylthio-trans-2'-oxtenyl)cyclopentane-1-carboxylate was dissolved in 10 ml of methylene chloride, and 203 mg (1 mmol) of 85% m chloroperbenzoic acid was added to the solution followed by stirring for 3 hours at room temperature. After disappearance of the starting material in the reaction mixture by thin layer chromatography, ammonium gas was bubbled into the reaction mixture and the ammonium salt formed was separated by filtration. The filtrate was washed with water, dried over anhydrous magnesium sulfate and filtered. The solvent was then removed from the filtrate by distillation under reduced pressure, and the residue was purified by silica gel column chromatography using a mixture of ethyl acetate and n-hexane (1:1 by volume) as an eluent to obtain 220 mg (60% yield) of methyl 2-oxo-5-(1'-benzenesulfinyl-trans-2'-octenyl)cyclopentane-1-carboxylate as a viscous oily substance.

Infrared Absorption Spectrum (cm$^{-1}$): 1763, 1755, 1727, 1085, 1035, 996, 980.

NMR Absorption Spectrum (CCl$_4$): 0.85 (t, J=5 Hz, 3H), 1.00–2.75 (m, 13H), 2.75–3.52 (m, 2H), 3.52–3.90 (m, 3H), 4.65–5.72 (m, 2H), 7.10–7.70 (m, 5H).

EXAMPLE 12

580 mg (1.3 mmol) of 2-(6'-methoxycarbonylhexyl)-3-(1'-phenylthio-trans-2'-octenyl)cyclopentanone was dissolved in 15 ml of methylene chloride, and 2.65 mg (1.3 mmol) of 85% m-chloroperbenzoic acid was added to the solution followed by stirring overnight under cooling with ice-water. After bubbling ammonia gas into the mixture, the ammonium salt formed was removed by filtration and the filtrate was washed with water, dried over anhydrous magnesium sulfate and filtered. The filtrate was concentrated under reduced pressure, and the residue was purified by silica gel column chromatography to obtain 350 mg (59% yield) of 3-(1'-benzenesulfinyl-trans-2'-octenyl)-2-(6'-methoxycarbonylhexyl)cyclopentanone.

Infrared Absorption Spectrum (cm$^{-1}$): 1755, 1740, 1045.

REFERENCE EXAMPLE 5

210 mg (0.57 mmol) of methyl 2-oxo-5-(1'benzenesulfinyltrans-2'-octenyl)cyclopentane-1-carboxylate was dissolved in 15 ml of absolute methanol, and 140 mg (1.14 mmol) of trimethyl phosphite was added to the solution followed by stirring for 3 hours at room temperature. After disappearance of the starting material in the reaction mixture was confirmed by thin-layer chromatography, methanol was removed by distillation under reduced pressure. The residue was then purified by silica gel chromatography using a mixture of ethyl acetate and n-hexane (3:7 by volume) as an eluent to obtain 130 mg (84% yield) of methyl 5-(3'-hydroxy-trans-1'-octenyl)-2-oxo-cyclopentane-1-carboxylate.

Infrared Absorption Spectrum (cm$^{-1}$): 3440, 1760, 1730, 975.

NMR Absorption Spectrum (CCl$_4$) δ: 0.86 (t, J=6 Hz, 3H), 1.04–2.66 (m, 14H), 2.84–3.43 (m, 1H), 3.68 (s, 3H), 3.89–4.14 (m, 1H), 5.34–5.80 (m, 2H).

While the invention has been described in detail with reference to specific embodiments thereof, it will be apparent to one skilled in the art various changes and modifications can be made therein without departing from the spirit and the scope thereof.

What is claimed is:

1. A process for preparing a compound of the formula (IId)

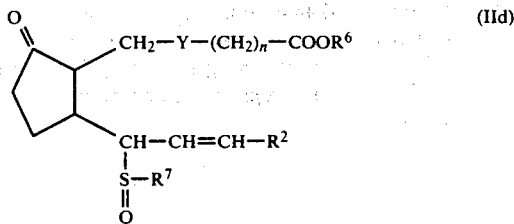
(IId)

wherein $R^2$ represents a substituted or unsubstituted alkyl group having 1 to 8 carbon atoms, $R^6$ represents a hydrogen atom or an alkyl group having 1 to 4 carbon atoms, $R^7$ represents an alkyl group having 1 to 4 carbon atoms or an aryl group, Y represents a —$CH_2CH_2$— group or a —CH=CH— group, and n is an integer of 0 to 6, which comprises subjecting an α-diazo-β-keto ester compound of the formula (III)

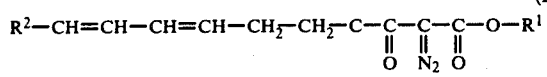
(III)

wherein $R^2$ is as defined above, and $R^1$ represents an alkyl group having 1 to 4 carbon atoms or an aryl group, to a carbene or carbenoid formation either by a catalytic reaction in the presence of a trace amount of a metal or metal salt catalyst or a photodecomposition through exposure to light to produce a 6-alkenylbicyclo[3.1.0]hexanone compound of the formula (I)

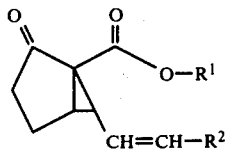
(I)

wherein $R^1$ and $R^2$ are as defined above, reacting the thus obtained 6-alkenyl-bicyclo[3.1.0]hexanone compound at from about 0° to about 100° C. with approximately equimolar amount of a mercaptan compound of the formula (V)

$R^7$-SH (V)

wherein $R^7$ is as defined above, in the presence of a base to produce a cyclopentanone sulfide compound of the formula (IIa)

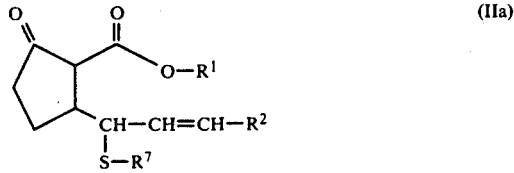
(IIa)

wherein $R^1$, $R^2$ and $R^7$ are as defined above, reacting the thus obtained cyclopentanone compound at from about −80° to about 150° C. with approximately equimolar amount of an alkylating agent of the formula (VI)

$Z$-$CH_2$-Y-$(CH_2)_n$-$COOR^6$ (VI)

wherein $R^6$, Y and n are as defined above, and Z represents a halogen atom, a tosyloxy group or an acyloxy group, in the presence of a base to produce a compound of the formula (IIb)

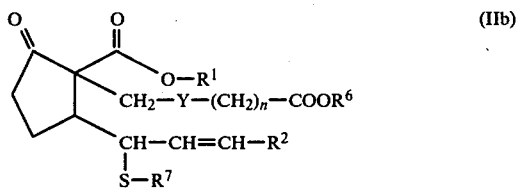
(IIb)

wherein $R^1$, $R^2$, $R^6$, $R^7$, Y and n are as defined above, subjecting the thus obtained compound of the formula (IIb) to either (1) heat-treatment at a temperature of about 50 to about 200° C. in the presence of an alkali metal compound and an inert polar solvent, or (2) an acid or alkali hydrolysis at a temperature of about 0° to about 150° C. followed by heat-treatment at a temperature of about 50° to about 200° C. to produce a compound of the formula (IIc)

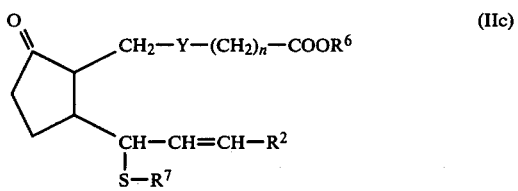
(IIc)

wherein $R^2$, $R^6$, $R^7$, Y and n are as defined above, and oxidizing the thus obtained compound of the formula (IIc) with an oxidizing agent at a temperature of about −80° to about 100° C. in an inert solvent.

2. The process as claimed in claim 1, wherein said compound of the formula (I) is selected from the group consisting of
methyl exo-6-(trans-1'-heptenyl)-2-oxo-bicyclo[3.1.0]hexane-1-carboxylate,
ethyl exo-6-(trans-1'-heptenyl)-2-oxo-bicyclo[3.1.0]hexane-1-carboxylate,
methyl exo-6-(trans-1'-propenyl)-2-oxo-bicyclo[3.1.0]hexane-1-carboxylate, and
ethyl exo-6-(trans-1'-propenyl)-2-oxo-bicyclo[3.1.0]hexane-1-carboxylate.

3. The process as claimed in claim 1, wherein said compound of the formula (IIa) is selected from the group consisting of
methyl 2-oxo-5-(1'-phenylthio-trans-2'-butenyl)cyclopentane-1-carboxylate,
methyl 2-oxo-5-(1'-phenylthio-trans-2'-octenyl)cyclopentane-1-carboxylate,
ethyl 2-oxo-5-(1'-phenylthio-trans-2'-octenyl)cyclopentane-1-carboxylate,
methyl 2-oxo-5-(1'-tolylthio-trans-2'-octenyl)-cyclopentane-1-carboxylate,
methyl 5-(1'-methylthio-trans-2'-octenyl)-2-oxocyclopentane-1-carboxylate, and
methyl 5-(4'-methyl-1'-phenylthio-trans-2'-octenyl)-2-oxo-cyclopentane-1-carboxylate.

4. The process as claimed in claim 1 wherein the metal or metal salt catalyst is selected from the group consisting of copper powder, copper bronze, copper halides, copper sulfate, acetyl-acetonate-copper, copper phosphine complex, silver oxide, and silver nitrate.

5. The method as claimed as in claim 1 wherein said catalytic reaction or said photodecomposition reaction is carried out in an inert solvent in an inert atmosphere.

6. The method as claimed in claim 1 wherein in the reaction to produce said compounds (IIa), the base is selected from alkali metal hydroxides, alkali metal alkoxides or organic amines.

7. The method as claimed in claim 1 wherein said compound of the formula (VI) is methyl 7-chloro-heptanoate, methyl 7-bromoheptanoate, methyl 7iodoheptanoate, ethyl 7-iodoheptanoate, methyl 7-bromo-5-heptenoate, methyl 7-iodo-5-heptenoate, or 1-iodo-6-(2'-tetrahydropyranyloxycarbonyl)-hexane.

8. The method as claimed in claim 1 wherein in the reaction to produce the compound of the formula (IIb) from a compound of the formula (IIa), the base which is used is an alkali metal carbonate, alkali metal hydroxide, alkali metal hydride, alkali metal alkoxide, or an organic amine.

9. The method as claimed in claim 1 wherein the reaction to form the compound of the formula (IIb) from the compound of the formula (IIa) is carried out in an inert organic solvent.

10. The method as set forth in claim 9 wherein the inert organic solvent is an alcohol, an ether, tetrahydrofuran, benzene, toluene, xylene, dimethylformamide, acetonitrile, or dimethyl sulfoxide.

11. A method as claimed in claim 1 wherein the compound of the formula (IIb) is methyl 1-(6'methoxycarbonylhexyl)2-oxo-5-(1'-phenylthio-2'-trans-octenyl)cyclopentane-1-carboxylate, methyl 1-(6'methoxycarbonyl-2'-hexenyl)-2-oxo-5-(1'-phenyl-thio-trans-octenyl)-cyclopentane-1-carboxylate, methyl 1-(6'-ethoxycarbonylhexyl)-2-oxo-5-(1'-tolylthio-trans-2'-octenyl)-cyclopentane-1-carboxylate, methyl 1-(6'-methoxycarbonylhexyl)-5-(4'-methyl-1'-phenylthio-trans-2'octenyl)-2-oxo-cyclopentane-1-carboxylage, or methyl 1-(6'-methoxycarbonylhexyl)-5-(1'-methylthio-trans-2'-octenyl)-2-cyclopentane-1-carboxylate.

12. The method as claimed in claim 1 wherein the alkali metal compound used in the step to produce the compound of (IIc) is an alkali metal iodide, alkali metal hydrate or alkali metal cyanide.

13. The method as claimed in claim 1 wherein in the step to produce the compound of the formula (IIc), wherein acid or alkali hydrolysis is carried out, the acid used is an inorganic acid or an organic acid and the base used is an alkali metal hydroxide or an alkali metal carbonate.

14. A method as claimed in claim 1 wherein said compound of the formula (IIc) is 2-(6'-methoxycarbonylhexyl)-3-(1'-phenylthio-2'-trans-octenyl)cyclopentanone, 2-(6'-methoxycarbonyl-2'-hexenyl)-3-(1'-phenylthio-trans-2'-octenyl)cyclopentanone, 2-(6'-ethoxycarbonylhexyl)-3-(1'-tolylthio-trans-2'octenyl)-cyclopentanone, 2-(6'-methoxycarbonylhexyl)-3-(4'-methyl-1'-phenylthio-2'-trans-octenyl)cyclopentanone, or 2-(6'-methoxy-carbonylhexyl)-3-(1'-methylthio-trans-2'-octenyl)cyclopentanone, etc.

15. The method as claimed in claim 1 wherein the oxydizing agent is sodium iodate, hydrogen peroxide, oxygen, ozone, manganese dioxide, selenium dioxide, chromic acid, nitric acid, dinitrogen tetraoxide, peracetic acid, perbenzoic acid, or m-chloroperbenzoic acid, iodosobenzene.

16. The method as claimed in claim 1 wherein said compound of the formula (IId) is 3-(1'-benzenesulfinyl-trans-2'-octenyl)-2-(6'-methoxycarbonylhexyl)cyclopentanone, 3-(1'-benzenesulfinyl-trans-2'-octenyl)-2-(6'-methoxycarbonyl-2'-hexenyl)cyclopentanone, 3-(1'-benzenesulfinyl-2'-trans-octenyl)-2-(6'ethoxy-carbonylhexyl)cyclopentanone, 3-(1'-benzenesulfinyl-4'-methyl-trans-2'-octenyl)-2-(6'-methoxycarbonylhexyl)cyclopentanone, or 3-(1'-methanesulfinyl-trans-2'-octenyl)-2-(6'-methoxycarbonylhesyl)cyclopentanone.

17. A process for preparing a compound of the formula (IIe)

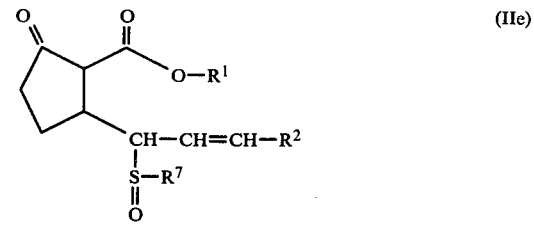

wherein $R^1$ represents an alkyl group having 1 to 4 carbon atoms or an aryl group, $R^2$ represents a substituted or unsubstituted alkyl group having 1 to 8 carbon atoms, and $R^7$ represents an alkyl group having 1 to 4 carbon atoms or an aryl group, which comprises subjecting an α-diazo-β-keto ester compound of the formula (III)

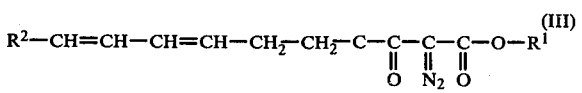

wherein $R^2$ is as defined above, and $R^1$ represents an alkyl group having 1 to 4 carbon atoms or an aryl group to a carbene or carbenoid formation either by catalytic reaction in the presence of a trace amount of a metal or metal salt catalyst or a photo-decomposition through exposure to light to produce a 6-alkenyl bicyclo [3.1.0]hexanone compound of the formula (I)

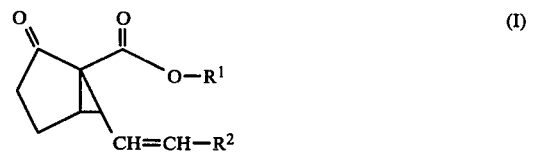

wherein $R^1$ and $R^2$ are as defined above, reacting the thus obtained 6-alkenyl-bicyclo[3.1.0]hexanone compound at from about 0° C. to about 100° C. with approximately equimolar amount of a mercaptan compound of the formula (V)

$$R^7-SH \qquad (V)$$

wherein $R^7$ is as defined above, in the presence of a base to produce a cyclopentanone sulfide compound of the formula (IIa)

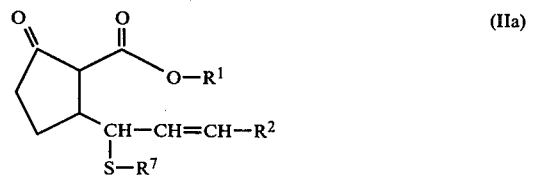

wherein $R^1$, $R^2$ and $R^7$ are as defined above, and oxidizing the thus obtained cyclopentanone sulfide compound with an oxidizing agent in an inert solvent at from about −80° to about 100° C.

18. The process as claimed in claim 17, wherein said compound of the formula (I) is selected from the group consisting of
- methyl exo-6-(trans-1'-heptenyl)-2-oxo-bicyclo[3.1.0-]hexane-1-carboxylate,
- ethyl exo-6-(trans-1'-heptenyl)-2-oxo-bicyclo[3.1.0]hexane-1-carboxylate,
- methyl exo-6-(trans-1'-propenyl)-2-oxo-bicyclo[3.1.0-]hexane-1-carboxylate, and
- ethyl exo-6-(trans-1'-propenyl)-2-oxo-bicyclo[3.1.0-]hexane-1-carboxylate.

19. The process as claimed in claim 17, wherein said compound of the formula (IIa) is selected from the group consisting of
- methyl 2-oxo-5-(1'-phenylthio-trans-2'-butenyl)cyclopentane-1-carboxylate,
- methyl 2-oxo-5-(1'-phenylthio-trans-2'-octenyl)cyclopentane-1-carboxylate,
- ethyl 2-oxo-5-(1'-phenylthio-trans-2'-octenyl)cyclopentane-1-carboxylate,
- methyl 2-oxo-5-(1'-tolylthio-trans-2'-octenyl)-cyclopentane-1-carboxylate,
- methyl 5-(1'-methylthio-trans-2'-octenyl)-2-oxo-cyclopentane-1-carboxylate, and
- methyl 5-(4'-methyl-1'-phenylthio-trans-2'-octenyl)-2-oxo-cyclopentane-1-carboxylate.

20. The process as claimed in claim 17 wherein the metal or metal salt catalyst is selected from the group consisting of copper powder, copper bronze, copper halides, copper sulfate, acetyl-acetonate-copper, copper phosphine complex, silver oxide, and silver nitrate.

21. The method as claimed in claim 17 wherein said catalytic reaction or said photodecomposition reaction is carried out in an inert solvent in an inert atmosphere.

22. The method as claimed in claim 17 wherein in the reaction to produce said compounds (IIa), the base is selected from alkali metal hydroxides, alkali metal alkoxides or organic amines.

23. The method as claimed in claim 17 wherein the oxydizing agent is sodium iodate, hydrogen peroxide, oxygen, ozone, manganese dioxide, selenium dioxide, chromic acid, nitric acid, dinitrogen tetraoxide, peracetic acid, perbenzoic acid, or m-chloroperbenzoic acid, iodosobenzene.

24. The method as claimed in claim 17 wherein the compound of the formula (IIe) is methyl-2-oxo-5-(1'benzenesulfinyl-trans-2'-octenyl)cyclopentane-1-carboxylate, ethyl 2-oxo-5-(1'-benzene-sulfinyl-trans-2'-octenyl)cyclopentane-1-carboxylate, methyl 2-oxo-5-(1'-toluenesulfinyl-trans-2'-octenyl)cyclopentane-1-carbonxylate, or methyl 2-oxo-5-(1'-methanesulfinyl-trans-2'-octenyl)cyclopentane-1-carboxylate.

* * * * *